United States Patent
Geller et al.

(10) Patent No.: US 7,129,353 B2
(45) Date of Patent: Oct. 31, 2006

(54) METHOD FOR PRODUCING 4,6-DICHLORO-5-FLUOROPYRIMIDINE

(75) Inventors: Thomas Geller, Odenthal (DE); Holger Weintritt, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/517,505

(22) PCT Filed: Jun. 3, 2003

(86) PCT No.: PCT/EP03/05778

§ 371 (c)(1),
(2), (4) Date: Aug. 24, 2005

(87) PCT Pub. No.: WO03/106432

PCT Pub. Date: Dec. 24, 2003

(65) Prior Publication Data

US 2006/0014952 A1    Jan. 19, 2006

(30) Foreign Application Priority Data

Jun. 13, 2002  (DE) ................. 102 26 220

(51) Int. Cl.
*C07D 239/24*  (2006.01)
*C07D 239/30*  (2006.01)

(52) U.S. Cl. .................... 544/319; 544/334
(58) Field of Classification Search ............. 544/319, 544/334

See application file for complete search history.

(56) References Cited

U.S. PATENT DOCUMENTS

| 3,365,452 A | 1/1968 | Weidinger et al. .......... 260/248 |
| 5,723,612 A | 3/1998 | Huber et al. ................ 544/334 |
| 6,194,418 B1 * | 2/2001 | Seitz et al. ................. 514/256 |
| 2002/0042514 A1 | 4/2002 | Doyle et al. ................ 544/334 |

FOREIGN PATENT DOCUMENTS

| DE | 196 42 533 A1 | 4/1998 |
| EP | 1 077 210 A | 2/2001 |
| WO | 95/29166 A | 11/1995 |
| WO | 00/46212 | 8/2000 |

* cited by examiner

*Primary Examiner*—Venkataraman Balasubramanian
(74) *Attorney, Agent, or Firm*—Richard E. L. Henderson

(57) ABSTRACT

The invention relates to a novel process for preparing 4,6-dichloro-5-pyrimidine.

7 Claims, No Drawings

METHOD FOR PRODUCING 4,6-DICHLORO-5-FLUOROPYRIMIDINE

The present patent application has been filed under 35 U.S.C. 371 as a national stage application of PCT/EP2003/005778, filed Jun. 3, 2003, which was published in German as International Patent Publication WO 2003/106432 on Dec. 24, 2003, which is entitled to the right of priority of German Patent Application 102 26 220.9, filed Jun. 13, 2002.

The invention relates to a novel process for preparing 4,6-dichloro-5-fluoro-pyrimidine.

4,6-Dichloro-5-fluoropyrimidine is an intermediate which can be used, for example, for the preparation of crop protection agents (cf. EP-A-0 882 043).

A process for preparing 4,6-dichloro-5-fluoropyrimidine has already been described in EP-A- 1 077 210.

In this process, 4,6-dihydroxy-5-fluoropyrimidine or its alkali metal salt is reacted with phosphorus oxychloride. The resulting reaction mixture 1 is reacted with chlorine in the presence of phosphorus trichloride. The product 4,6-dihydroxy-5-fluoropyrimidine is removed from phosphorus oxychloride in the resulting reaction mixture. A disadvantage of this process is the recycling of phosphorus oxychloride by a complicated distillation and also the long reaction time.

The prior art discloses processes for chlorinating hydroxypyrimidines. In these processes, unsubstituted or substituted hydroxypyrimidines are reacted with chlorine and phosphorus trichloride or phosphorus oxychloride to give the corresponding chlorine-substituted pyrimidines (cf., for example, DE-A1-196 42533, DE-A1-195 242 83).

In contrast, the use of phosgene as a chlorinating reagent for preparing chlorine-substituted pyrimidines from hydroxy-substituted pyrimidines is unusual.

A process for preparing 4,6-dichloropyrimidine which is unsubstituted in the 5-position is described in WO 95/29166. In this process, 4,6-dihydroxypyrimidine is reacted with phosgene in the presence of a base and optionally in the presence of a solvent.

A further process for preparing unsubstituted 4,6-dichloropyrimidine is described in WO 02/00628. In this process, 4,6-dihydroxypyrimidine is reacted with phosgene in the presence of a quaternary ammonium salt or quaternary phosphonium salt as a catalyst.

WO 00/46212 discloses a process for preparing 4-chloropyrimidine substituted in the 2-position. In this process, a 4-hydroxypyrimidine substituted in the 2-position is reacted with phosgene in the presence of a phosphine or phosphine oxide as a catalyst and optionally of a phase transfer catalyst.

In this process, the starting compounds used are hydroxypyrimidines which are either unsubstituted or substituted in the 2-position.

Only FR-A-1310810 discloses a process which enables the chlorination using phosgene of hydroxypyrimidines which are substituted in the 5-position by aryl or alkyl. As an example, the conversion of 5-phenyl-4,6-dihydroxypyrimidine to 5-phenyl-4,6-dichloropyrimidine in o-dichlorobenzene as a solvent and dimethyl-formamide as a catalyst is described. A disadvantage of this process is that phosgene forms a carcinogenic intermediate with dimethylformamide.

No process is known which allows the chlorination with phosgene of hydroxy-pyrimidines substituted in the 5-position by halogen.

It is an object of the present invention to provide a process for preparing 4,6-dichloro-5-fluoropyrimidine which enables preparation on the industrial scale in better yields, higher purity and shorter reaction times. In particular, a process should be found which avoids a complicated distillation and the recycling or disposal of phosphorus oxychloride.

It has now been found that, surprisingly, the 5-fluoro-substituted 4,6-dichloropyrimidine of the formula

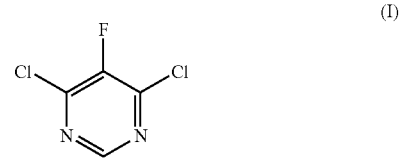

is obtained when 4,6-dihydroxy-5-fluoropyrimidine of the formula (II) or its alkali metal salt

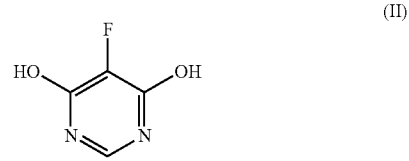

is reacted with phosgene in the presence of a solvent, optionally in the presence of a catalyst and optionally in the presence of a phase transfer catalyst.

The reaction can, for example, be carried out in chlorobenzene, nitrobenzene, aceto-nitrile or dichloroethane as a solvent.

It is particularly surprising that when the process according to the invention is carried out in nitrobenzene as a solvent, 4,6-dichloro-5-fluoropyrimidine can be obtained even without the addition of a catalyst or catalyst/phase transfer catalyst. In a preferred variant, the reaction is therefore carried out in nitrobenzene as a solvent.

In a particularly preferred variant, the reaction is carried out in the presence of nitrobenzene as a solvent and in the presence of 4-dimethylaminopyridine (DMAP) as the sole catalyst.

A distinct advantage of the process according to the invention is that 4,6-dichloro-5-fluoropyrimidine is obtained in substantially higher yields compared to the only existing preparative process (cf. EP-A-1 077 210).

A further advantage is that the proportion of by-products is very low.

In the product isolation, a distinct advantage is that when carrying out the process in nitrobenzene as a solvent and 4-dimethylaminopyridine (DMAP) as a catalyst, the 4,6-dichloro-5-fluoropyrimidine as the first component of the reaction mixture can be distilled off and the distillation residue composed of nitrobenzene, DMAP and any secondary components present can be reused for a further reaction.

4,6-Dihydroxy-5-fluoropyrimidine of the formula (II) is known and can be prepared by simple processes (cf. EP-A-1 079 210).

All other starting compounds are common trade products or can be prepared from them by simple processes.

Phosgene can be used in gaseous or in dissolved form.

Useful diluents for carrying out the process according to the invention include, in addition to nitrobenzene, halogenated hydrocarbons, for example chlorobenzene, dichlorobenzene, dichloromethane, chloroform, tetrachloromethane, dichloroethane or trichloroethane; nitriles, for example acetonitrile, propionitrile, n-butyronitrile, i-butyronitrile or benzonitrile. Preference is given to chlorobenzene, nitrobenzene, acetonitrile or dichloroethane as solvents. Particular preference is given to using nitrobenzene.

Useful catalysts of the process according to the invention include triarylphosphine oxides, for example triphenylphosphine oxide; trialkylphosphine oxides, for example tri-n-octylphosphine oxide, tri-n-butylphosphine oxide; triarylphosphines, for example triphenylphosphine; trialkylphosphines, for example tri-n-octylphosphine; substituted ureas, for example tetrabutylurea, tetramethylurea; N,N-dimethyl-formamide; or amines, for example 4-dimethylaminopyridine (DMAP) or piperidine. Preference is given to using DMAP.

The process according to the invention is carried out optionally in the presence of a suitable phase transfer catalyst. These include, for example and with preference, quaternary ammonium and phosphonium salts, crown ethers, for example dibenzo-18-crown-6, guanidinium salts, for example hexaalkylguanidium chloride, and also polyethylene glycol derivatives.

Examples of preferred quaternary ammonium and quaternary phosphonium catalysts include compounds of the formula (III)

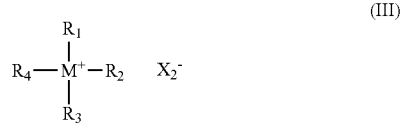

where $R_1$, $R_2$, $R_3$ and $R_4$ are each independently branched or linear $C_1$–$C_{16}$-alkyl, or benzyl, capryl, phenyl or trityl, each of which is optionally substituted by nitro, methyl, ethyl, n- or i-propyl, n-, i-, s- or t-butyl, methoxy, ethoxy, difluoromethyl, trifluoromethyl, allyl or propargyl, M is P or N, and $X_2$ is halide, hydrogen sulphate, tetrafluoroborate, trifluoromethanesulphonate, acetate, perchlorate, dihydrogen phosphate or nitrate.

$C_1$–$C_{16}$-Alkyl is generally representative of saturated, straight-chain or branched $C_1$–$C_{16}$-hydrocarbon chains, although preference is given, unless otherwise stated, to hydrocarbon chains having from 1 to 6 carbon atoms such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

These include, for example, tetrabutylammonium bromide, chloride, hydrogen sulphate or sulphate, methyltrioctylammonium bromide or chloride, hydrogen sulphate or sulphate, or 4-dimethylamino-N-(2-ethylhexyl)pyridinium bromide or chloride, hydrogen sulphate or sulphate, quaternary phosphonium salts, for example tributyltetradecylphosphonium bromide or chloride, tetraphenylphosphonium bromide or chloride.

Particularly preferred phase transfer catalysts are tetrabutylammonium chloride, tetramethylammonium chloride, tetraoctylammonium chloride and tricaprylmethyl-ammonium chloride (ALIQUAT 336).

The reaction temperatures when carrying out the process according to the invention can be varied within a relatively wide range. In general, operation is effected within a temperature range from 40° C. to the reflux temperature of the particular mixture, preferably within a temperature range of from 60 to 120° C.

The process according to the invention is carried out at atmospheric pressure or at elevated pressure, in particular at pressures of from 1 to 4 bar, preferably at pressures of from atmospheric pressure to 3 bar.

To carry out the process according to the invention for preparing the compounds of the formula (I), generally from 2 to 20 mol, preferably from 2 to 10 mol, more preferably from 2 to 6 mol, of phosgene are used per mole of the compound of the formula (II).

To carry out the process according to the invention for preparing the compound of the formula (I), generally from 0 to 30 mol %, preferably from 0 to 10 mol %, more preferably from 0 to 5 mol %, of the catalyst are used per mole of the compound of the formula (II).

To carry out the process according to the invention for preparing the compound of the formula (I), generally 0–30 mol %, preferably 0–10 mol %, more preferably 0–5 mol %, of the phase transfer catalyst are used per mole of the compound of the formula (II).

To carry out the process according to the invention, the procedure is generally as follows:

The compound of the formula (II) is initially charged in a solvent, optionally with a catalyst. Phosgene is introduced or optionally added in liquid form and the reaction mixture is heated for between one and 24 hours. There then follows a distillative workup.

The process according to the invention is used to prepare 4,6-dichloro-5-fluoro-pyrimidine (I) which is an important intermediate for the preparation of pesticides. The process according to the invention provides 4,6-dichloro-5-fluoro-pyrimidine in constant high purities and very good yields. The novel process therefore eases the preparation of existing and novel pesticides.

The examples which follow serve to illustrate the invention. However, the invention is not limited to the examples.

EXAMPLES

Examples 1 to 38

General Procedure 1 for the Preparation of 4,6-dichloro-5-fluoropyrimidine from 4,6dihydroxy-5-fluoropyrimidine

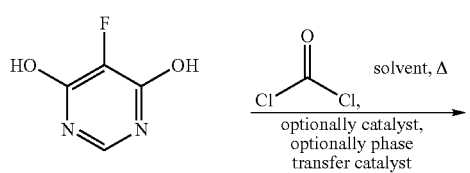

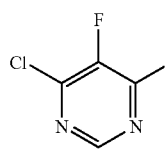

In a three-necked flask equipped with a stirrer, internal thermometer and also a reflux condenser cooled to −30° C. and having a fitted gas outlet cap and connection to a scrubbing tower, 1.30 g (10 mmol) of 4,6-dihydroxy-5-fluoropyrimidine are initially charged and optionally admixed with catalyst (type and equivalents: see table). After adding 40 g of a 15% solution of phosgene in a solvent (=6 eq. of phosgene, solvent: see table), the mixture is heated at a bath temperature of 95° C. (chlorobenzene, nitrobenzene) or 75° C. (acetonitrile) and stirred under phosgene reflux for 20 hours. The yield is determined by weighing and purity determinations of the reaction mixture against a standard (pure substance, GC-MS silylated).

TABLE 1

| Example | Solvent | Catalyst 1 (eq) | Catalyst 2 (eq) | Yield [% of theory] |
|---|---|---|---|---|
| 1 | Chlorobenzene | / | / | / |
| 2 | Chlorobenzene | Triphenylphosphine oxide (0.1) | / | 82 |
| 3 | Chlorobenzene | Triphenylphosphine oxide (0.1) | $(n-C_4H_9)_4NCl$ (0.1) | 88 |
| 4 | Chlorobenzene | Triphenylphosphine oxide (0.1) | $(n-C_8H_{17})_4NCl$ (0.1) | 89 |
| 5 | Chlorobenzene | Triphenylphosphine oxide (0.1) | $(CH_3)_4NCl$ (0.1) | 78 |
| 6 | Chlorobenzene | Triphenylphosphine oxide (0.1) | Aliquat 336 (0.1) | 88 |
| 7 | Chlorobenzene | Triphenylphosphine oxide (0.1) | Aliquat 175 (0.1) | 76 |
| 8 | Chlorobenzene | Triphenylphosphine oxide (0.1) | 4-Dimethylaminopyridine (0.1) | 72 |
| 9 | Chlorobenzene | / | 4-Dimethylaminopyridine (0.1) | 74 |
| 10 | Chlorobenzene | / | Tetrabutylurea (0.1) | 84 |
| 11 | Chlorobenzene | Tributylphosphine oxide (0.1) | / | 86 |
| 12 | Chlorobenzene | Trioctylphosphine oxide (0.1) | / | 88 |
| 13 | Chlorobenzene | Trioctylphosphine oxide (0.1) | Aliquat 336 (0.1) | 81 |
| 14 | Chlorobenzene | Triphenylphosphine (0.1) | $(n-C_4H_9)_4NCl$ (0.1) | 87 |
| 15 | Chlorobenzene | / | N,N-Dibutylformamide (0.1) | 62 |
| 16 | Chlorobenzene | Triphenylphosphine oxide (0.1) | Tetra-n-butylurea (0.1) | 91 |
| 17 | Chlorobenzene | / | Urea (0.1) | 43 |
| 18 | Chlorobenzene | / | Tetra-n-methylurea (0.1) | 72 |
| 19 | Chlorobenzene | / | Tetra-n-butylurea (0.1) | 75 |
| 20 | Chlorobenzene | / | 1,3-Dimethylimidazolin-2-one (0.1) | 52 |
| 21 | Chlorobenzene | / | N-Methylpyrrolidone (0.1) | 22 |
| 22 | Chlorobenzene | Tri-n-octylphosphine oxide (0.1) | Tetra-n-butylurea (0.1) | 90 |
| 23 | Nitrobenzene | / | / | 66 |
| 24 | Nitrobenzene | / | 4-Dimethylaminopyridine (0.1) | 93 |

TABLE 1-continued

| Example | Solvent | Catalyst 1 (eq) | Catalyst 2 (eq) | Yield [% of theory] |
|---|---|---|---|---|
| 25 | Nitrobenzene | / | 4-Dimethylaminopyridine (0.05) | 94 |
| 26 | Nitrobenzene | / | 4-Dimethylaminopyridine (0.025) | 94 |
| 27 | Nitrobenzene | / | 4-Dimethylaminopyridine (0.01) | 81 |
| 28 | Nitrobenzene | Triphenylphosphine oxide (0.1) | (n-$C_4H_9$)$_4$NCl (0.1) | 87 |
| 29 | Nitrobenzene | Tri-n-butylphosphine oxide (0.1) | / | 88 |
| 30 | Nitrobenzene | Tri-n-octylphosphine oxide (0.1) | / | 90 |
| 31 | Nitrobenzene | Triphenylphosphine oxide (0.1) | / | 88 |
| 32 | Nitrobenzene | Tri-n-octylphosphine oxide (0.1) | Tetramethylurea (0.1) | 84 |
| 33 | Nitrobenzene | / | Pyridine (0.1) | 79 |
| 34 | Nitrobenzene | / | Imidazole (0.1) | 83 |
| 35 | Acetonitrile | Triphenylphosphine oxide (0.1) | (n-$C_4H_9$)$_4$NCl (0.1) | 72 |
| 36 | Acetonitrile | Triphenylphosphine oxide (0.1) | 4-Dimethylaminopyridine (0.1) | 79 |
| 37 | Acetonitrile | / | Tetra-n-butylurea (0.1) | 55 |
| 38 | Acetonitrile | / | Teramethylurea (0.1) | 53 |

General Procedure 2 for the Preparation of 4,6-dichloro-5-fluoropyrimidine from 4,6dihydroxy-5-fluoropyrimidine

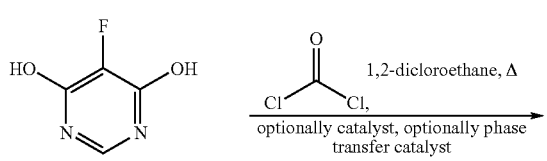

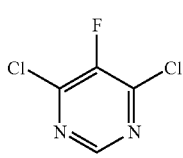

In a three-necked flask equipped with a stirrer, internal thermometer and also a reflux condenser cooled to −30° C. and having a fitted gas outlet cap and connection to a scrubbing tower, 6.5 g (50 mmol) of 4,6-dihydroxy-5-fluoropyrimidine are initially charged and admixed with catalyst (type and equivalents: see table). After adding 175 ml of 1,2-dichloroethane, 4 eq. of phosgene are introduced at approx. 70–80° C. and the mixture is stirred under phosgene reflux for 6 hours and subsequently without phosgene reflux (condenser switched off) for approx. 14 hours.

The yield is determined by weighing and purity determinations of the reaction mixture against standard (pure substance, GC-MS silylated).

TABLE 2

| Example | Solvent | Catalyst 1 (eq) | Catalyst 2 (eq) | Yield [% of theory] |
|---|---|---|---|---|
| 39 | 1,2-Dichloroethane | Triphenylphosphine oxide (0.1) | / | 65 |
| 40 | 1,2-Dichloroethane | Triphenylphosphine oxide (0.1) | Aliquat 336 (0.1) | 80 |
| 41 | 1,2-Dichloroethane | Triphenylphosphine oxide (0.1) | Tetraphenyl phosphonium chloride (0.1) | 83 |
| 42 | 1,2-Dichloroethane | Triphenylphosphine oxide (0.1) | $(CH_3)_4NCl$ (0.1) | 77 |
| 43 | 1,2-Dichloroethane | Triphenylphosphine oxide (0.1) | $(n-C_8H_{17})_4NCl$ (0.1) | 80 |
| 44 | 1,2-Dichloroethane | Triphenylphosphine oxide (0.1) | Aliquat 175 (0.1) | 77 |
| 45 | 1,2-Dichloroethane | 4-Dimethylaminopyridine 0.1 | / | 81 |
| 46 | 1,2-Dichloroethane | / | Tetrabutylurea (0.1) | 44 |

Example 47 for the Preparation of 4,6-dichloro-5-fluoropyrimidine from 4,6-dihydroxy-5-fluoropyrimidine

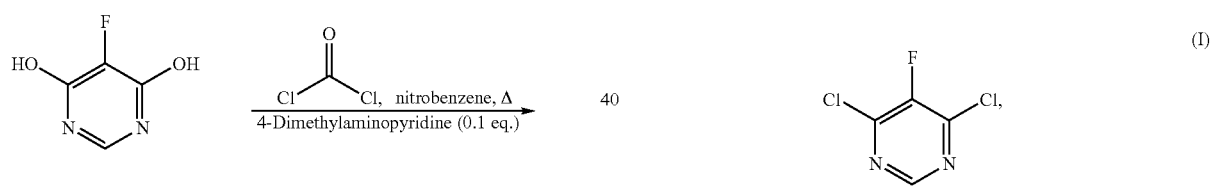

In a three-necked flask equipped with a stirrer, internal thermometer and a reflux condenser cooled to −30° C. and having a fitted gas outlet cap and connection to a scrubbing tower, 26 g (200 mmol) of 4,6-dihydroxy-5-fluoropyrimidine in 234 g of nitrobenzene are initially charged and admixed with 2.4 g of 4-dimethylamino-pyridine as the catalyst. Subsequently, 5 eq. of phosgene are introduced at approx. 85–70° C. over 3 hours and the mixture is stirred under phosgene reflux at 70° C. for 19 hours. Before the workup, excess phosgene is very substantially discharged with the condenser switched off (scrubbing tower). The product is obtained by distillation under reduced pressure. The yield is determined by weighing and purity determinations of the distillate against standard (pure substance, GC-MS silylated) and is 91% of theory.

What is claimed is:

1. A process for preparing the compound of formula (I)

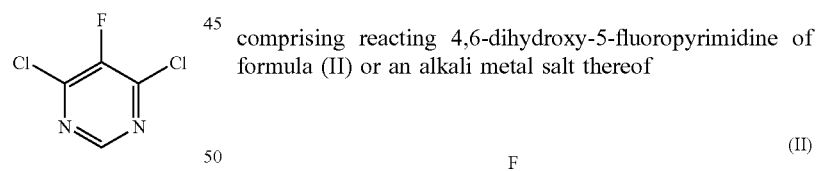

comprising reacting 4,6-dihydroxy-5-fluoropyrimidine of formula (II) or an alkali metal salt thereof with phosgene in the presence of nitrobenzene as solvent, optionally in the presence of a catalyst, and optionally in the presence of a phase transfer catalyst.

2. A process according to claim 1 in which the catalyst is 4-dimethylaminopyridine.

3. A process according to claim 1 carried out without a catalyst and without a phase transfer catalyst.

4. A process according to claim 1 carried out using 4-dimethylaminopyridine as a catalyst but without a phase transfer catalyst.

5. A process according to claim 1 carried out at temperatures from 40° C. up to the reflux temperature of the reaction mixture.

6. A process according to claim 1 in which from 2 to 20 mol of phosgene are used per mole of the compound of formula (II).

7. A process according to claim 1 in which from 0 to 30 mol% of the catalyst are used per mole of the compound of formula (II).

* * * * *